(12) United States Patent
Mohiuddin et al.

(10) Patent No.: US 11,255,762 B1
(45) Date of Patent: Feb. 22, 2022

(54) METHOD AND SYSTEM FOR CLASSIFYING SAMPLE DATA FOR ROBOTICALLY EXTRACTED SAMPLES

(71) Applicant: Specialty Diagnostic (SDI) Laboratories, Inc., Garden Grove, CA (US)

(72) Inventors: Ozman Mohiuddin, Redmond, WA (US); Brian T. Sutch, Pasadena, CA (US); Mohammad Ali Mahmood, Garden Grove, CA (US)

(73) Assignee: Specialty Diagnostic (SDI) Laboratories, Inc., Garden Grove, CA (US)

( * ) Notice: Subject to any disclaimer, the term of this patent is extended or adjusted under 35 U.S.C. 154(b) by 0 days.

(21) Appl. No.: 16/990,366

(22) Filed: Aug. 11, 2020

(51) Int. Cl.
*G01N 35/00* (2006.01)
*G01N 1/31* (2006.01)
(Continued)

(52) U.S. Cl.
CPC .............. *G01N 1/31* (2013.01); *B01L 3/508* (2013.01); *B01L 3/5029* (2013.01);
(Continued)

(58) Field of Classification Search
CPC ............. B01L 3/5029; B01L 2300/021; G01N 35/0099; G01N 35/00584;
(Continued)

(56) References Cited

U.S. PATENT DOCUMENTS

| 5,366,896 A | 11/1994 | Margrey et al. |
| 5,968,731 A | 10/1999 | Layne et al. |

(Continued)

FOREIGN PATENT DOCUMENTS

| WO | WO2017143182 | 8/2017 |
| WO | WO2019102282 | 5/2019 |

OTHER PUBLICATIONS https://fpf.org/2020/05/07/artificial-intelligence-and-the-covid-19-pandemic/.
International Search Report; PCT/US21/45309; dated Nov. 17, 2021; By: Authorized Officer Kari Rodriquez.

*Primary Examiner* — Jill A Warden
*Assistant Examiner* — Dwayne K Handy
(74) *Attorney, Agent, or Firm* — Caldwell Intellectual Property Law, LLC

(57) ABSTRACT

A method of classifying sample data for robotically extracted samples is disclosed. A specimen is received from a human subject with a potential infection of a first disease agents or a plurality of disease agents. The specimen includes genetic material collected from a human subject using a collection device and stored in a collection carrier. The specimen includes a unique identifier on the collection carrier. The unique identifier contains human subject descriptive data. The method classifies the human subject descriptive data to identify a second disease agent. The method extracts a sequence of genetic material from the specimen using an automated robot. The method determines a test result for the first disease agent as a function of the sequence of genetic material. A system comprising a computer device configured to classify sample data for robotically extracted samples is also disclosed.

20 Claims, 14 Drawing Sheets

(51) Int. Cl.
*B01L 3/00* (2006.01)
*C12Q 1/6806* (2018.01)
*G01N 1/02* (2006.01)
*G01N 1/00* (2006.01)

(52) U.S. Cl.
CPC ...... *C12Q 1/6806* (2013.01); *B01L 2200/025* (2013.01); *B01L 2200/0678* (2013.01); *B01L 2300/021* (2013.01); *B01L 2300/04* (2013.01); *B01L 2300/0809* (2013.01); *G01N 2001/007* (2013.01); *G01N 2001/028* (2013.01)

(58) Field of Classification Search
CPC ... G01N 35/00732; G01N 2035/00841; G01N 33/4833; G01N 2035/00831; G16H 50/20; A61B 5/7264
See application file for complete search history.

(56) References Cited

U.S. PATENT DOCUMENTS

| | | | |
|---|---|---|---|
| 6,702,988 B1 | 3/2004 | Sagona et al. | |
| 7,062,076 B1* | 6/2006 | Osborne et al. | G01N 2001/007 382/128 |
| 7,666,355 B2 | 2/2010 | Alavie et al. | |
| 8,107,693 B2 | 1/2012 | Osborne et al. | |
| 8,234,129 B2 | 7/2012 | Michon et al. | |
| 8,357,538 B2 | 1/2013 | Self et al. | |
| 8,862,448 B2 | 10/2014 | Holmes et al. | |
| 9,958,466 B2 | 5/2018 | Dalbert et al. | |
| 9,984,201 B2* | 5/2018 | Zhang | G16B 40/20 |
| 10,088,460 B2 | 10/2018 | DeWitte et al. | |
| 10,283,217 B2 | 5/2019 | Lui et al. | |
| 2004/0029260 A1* | 2/2004 | Hansen et al. | C12Q 1/68 435/287.2 |
| 2006/0275844 A1* | 12/2006 | Linke | G16H 70/60 435/7.23 |
| 2009/0092962 A1 | 4/2009 | Minekawa et al. | |
| 2009/0299645 A1* | 12/2009 | Colby | G16H 50/30 702/19 |
| 2009/0306543 A1 | 12/2009 | Slowey et al. | |
| 2010/0099083 A1 | 4/2010 | Raelson et al. | |
| 2011/0191768 A1 | 8/2011 | Smith | |
| 2015/0363563 A1 | 12/2015 | Hallwachs | |
| 2017/0175169 A1* | 6/2017 | Lee | G01N 33/54373 |
| 2018/0286497 A1 | 10/2018 | Bauer et al. | |
| 2020/0081023 A1 | 3/2020 | Holmes et al. | |
| 2020/0124868 A1 | 4/2020 | Carrascal De Las Heras et al. | |
| 2021/0042916 A1* | 2/2021 | Zhang | G06N 3/04 |

\* cited by examiner

METHOD AND SYSTEM FOR CLASSIFYING SAMPLE DATA FOR ROBOTICALLY EXTRACTED SAMPLES

FIELD OF THE INVENTION

The present invention generally relates to the field of laboratory sample testing. In particular, the present invention is directed to method and systems for automated biological sample testing.

BACKGROUND

The need for fast patient results is the key to controlling and maintaining infections rates low. Currently, the average turnaround time for a SARS-COV-2 test is one day for priority patients and 3-5 days for other populations. In a climate where faster turnaround times would help to isolate those who test positive quicker in order to prevent further spread, it would be an advantage to improve testing procedures to decrease turnaround times to obtain results as well as better data management to make better predictions as to potential "hot spots." Furthermore, it is important for labs to manage the data surrounding these samples in an efficient manner.

SUMMARY OF THE DISCLOSURE

In an aspect, a method of classifying sample data for robotically extracted samples is disclosed. A specimen is received from a human subject with a potential infection of a first disease agents or a plurality of disease agents. The specimen includes genetic material collected from a human subject using a collection device and stored in a collection carrier. The specimen includes a unique identifier on the collection carrier. The unique identifier contains human subject descriptive data. The method classifies the human subject descriptive data to identify a second disease agent. The method extracts a sequence of genetic material from the specimen using an automated robot. The method determines a test result for the first disease agent as a function of the sequence of genetic material.

In another aspect, a system of classifying sample data for robotically extracted samples is disclosed. The system includes a computing device configured to receive a specimen from a human subject with a potential infection of a first disease agent. The specimen includes genetic material collected from a human subject using a collection device and stored in a collection carrier. The specimen includes a unique identifier on the collection carrier. The unique identifier contains human subject descriptive data. Computing device is further configured to classify the human subject descriptive data to identify a second disease agent. Computing device is configured to generate an identity of a second disease agent. The system includes an optical scanning device configured to extract human subject descriptive data as a function of the unique identifier. The system includes an automated robot configured to extract a sequence of genetic material from the specimen. The system includes an analysis device configured to determine a test result for the first disease agent as a function of the sequence of genetic material.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIGS. 6A-6L are representative screenshots depicting various aspects of an exemplary human subject data collected in accordance with this disclosure.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to methods and systems of classifying sample data for samples extracted by using an automated robot. Testing includes specimens acquired from human subjects with each specimen containing genetic material for testing. Each sample includes an identifier which includes information about the human subject. Tests may be performed for one disease agent or a multiple disease agent where multiple disease agents may be identified by using a machine-learning model. If a positive result is obtained for a disease agent, an authorized person by human subject may be notified with an ability of the authorized person to have a conference event with, a medical professional such as without limitation a doctor.

Exemplary embodiments illustrating aspects of the present disclosure are described below in the context of several specific examples.

Figure 1:
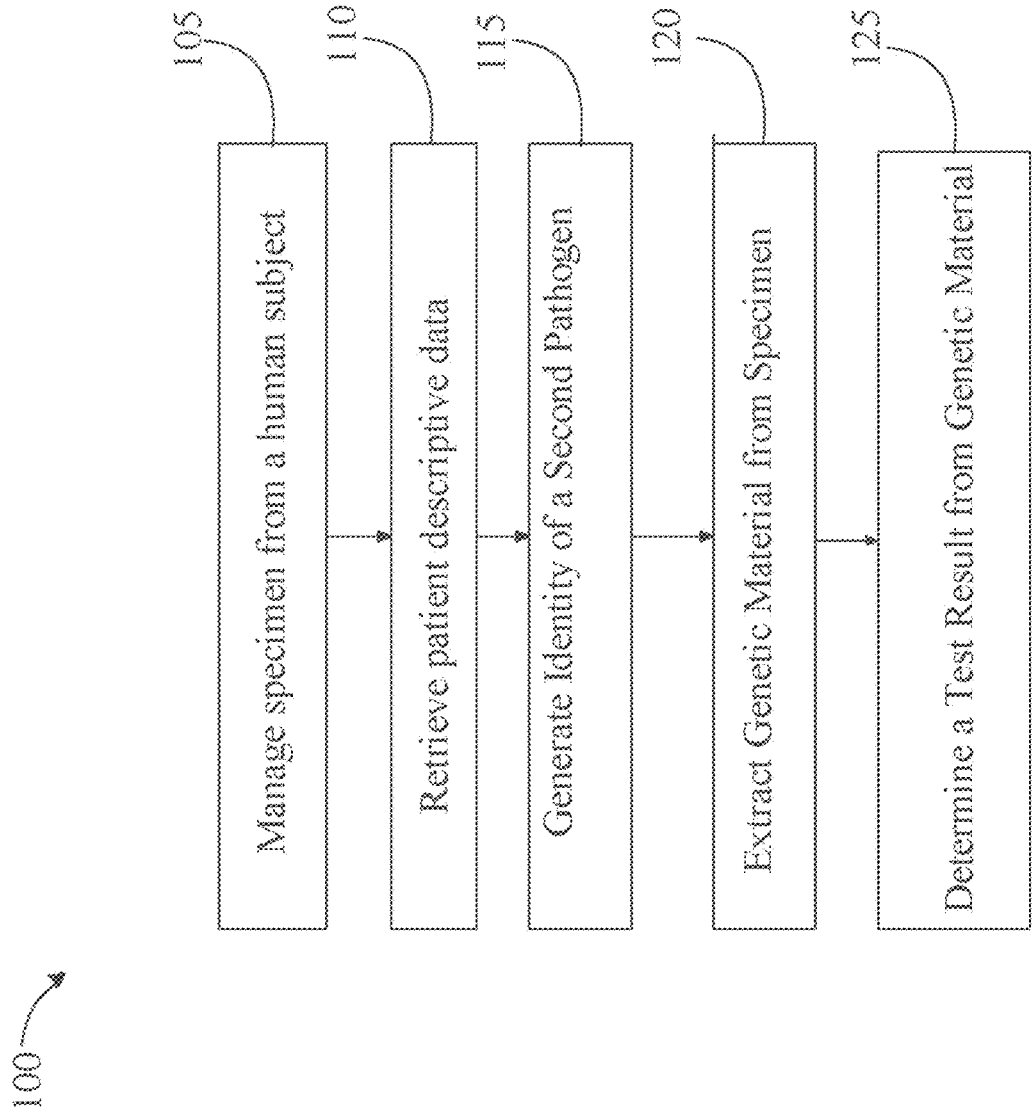
FIG. 1 is a flow diagram illustrating an exemplary embodiment of a method of automated biological sampling testing.

Referring FIG. 1, an exemplary method 100 of automated biological sample testing is illustrated. At step 105, the method includes receiving, by a computing device, a specimen from a human subject with a potential infection of a first disease agent. A potential infection may be caused by a plurality of disease agents. As defined in this disclosure, a "specimen" is an element of biological material derived from a human; a specimen may include any biological material. A specimen may contain viral proteins and/or genetic material (including without limitation ribonucleic acid (RNA) and/or deoxyribonucleic acid (DNA)), and/or other proteins associated with disease agents, where disease agents may include pathogens such as bacteria, archaea, protists, fungi, infections proteins such as prions, parasitic multicellular organisms such as nematodes including without limitation ascarids and/or filarial worms, flatworms including without limitation flukes and tapeworms, insectoid parasites such as without limitation botflies and/or screw worms, or the like, potentially indicative of an infection. Examples of biological material collected as specimens may include, but not limited to, blood, urine, fecal matter, tissues, organs, saliva, DNA/RNA, hair, nail clippings, or any other cell or fluids. Specimens may come from either an adult or a child. Specimens may be collected according to established protocols depending on the origin of the specimen. For example, collection of a specimen from the upper respiratory tract may use a nasopharyngeal swab method. Other examples of upper respiratory tract collection methods include, but are not limited to, a nasal mid-turbinate (NMT) swab and the nasopharyngeal wash, and/or the nasal wash/aspirate method. A lower respiratory tract sample may include the collection of sputum. Collection of a specimen from the throat region may involve the use of the oropharyngeal swab method. Other methods of collection, including without limitation extraction of fluids, tissue samples, biopsies, or the like may be employed to collect specimen.

Further referring to FIG. 1, specimen may be collected from a third-party provider. Examples of third-party providers include nursing homes, a hospital, a drive-through site, a pharmacy, a healthcare professional's office, an urgent care facility, and the like. Specimens may be preserved by refrigeration with ice or by snap freezing the sample in a dry ice/ethanol slurry. Specimens may be shipped for analysis using services such as the United States Postal Service, or private couriers such as Federal Express, United Parcel Service, or the like. A "disease agent" as defined in this disclosure, is any organism that causes disease, such as bacteria, virus, fungus, or protozoa. Disease agents may be transmitted by, for example, skin contact, bodily fluids, airborne particles, contact with bodily fluids, and by contact with a surface originally touched by an infected person. Examples of first disease agents include, but are not limited to Anthrax, Aspergillosis, Blastomycosis, Chicken pox, Adenovirus, Enterovirus, Rotavirus, Influenza, Coronaviridae such as, SARS-CoV-2 or any coronavirus, *Clostridium botulinum, Yersinia Pestis, Escherichia coli*, any other disease agent described in this disclosure, and the like. A specimen may include genetic material collected from a human subject using a collection device and stored in a collection carrier. As used in this disclosure, "genetic material" is material used to store genetic information in the nuclei or mitochondria or an organism's cell. Genetic material may include DNA and/or ribonucleic acid RNA. A potential infection may occur, for example, when a viral disease agent attaches to a specific host cell. Viral genetic information may then be inserted into a host cell where it starts to replicate, transcribe DNA into messenger RNA (mRNA) and translate mRNA into a viral protein. A new viral complex may then be released from the cell.

Still referring to FIG. 1, in an embodiment, collection device may include a swab and/or a transfer medium where the swab may be dipped in the transfer medium. Collection site to be used for testing may affect a type of swab used. Types of swabs that may be used include, but are not limited to, synthetic fiber swabs with plastic shafts such as COPAN FLOSwabs® 501CS01 for use in a nasopharyngeal site, a foam swab which may be used in nasal collection, and the like. Synthetic fibers used in swabs may include spun polyester fiber, spun rayon fiber, and the like. Swabs may be included as part of a disease agent testing kit. For example, a disease agent testing kit may include at least a swab, a sterile vessel that serves as a transport device, a transfer medium, a diagnostic requisition form, instructions, a unique identifier, and a bag for use to ship the sample to the testing laboratory. Sterile vessel may include without limitation a glass vial with a stopper, a plastic urine sample cup, a test tube, or the like. Transfer medium may include a buffer. The buffer may include a lysis buffer. As used in this disclosure, a "lysis" buffer is a buffer used for its ability to break up cells. Examples of a lysis buffer include, without limitation, an NP-40 lysis buffer, a sodium dodecyl sulfate (SDS) lysis buffer, an ammonium-chloride-potassium (ACK) lysing buffer, and the like. Transfer medium may be stable for a period ranging from at least 5 to 7 days. In a non-limiting example, a sample may be collected from a human subject by inserting a spun polyester swab with a plastic shaft into the nasopharyngeal cavity of a human subject. Post-sampling activities may include breaking plastic shaft in order to fit a sample into a sterile vessel which contains transfer medium. Swab may be dipped into transfer medium contained in transfer vessel. Transfer vessel may be sealed, and a unique identifier placed on sample, for instance in the form of a label, which may be alphanumeric and/or a machine-readable label such as without limitation a bar code and/or quick-read (QR) code. Sample and one or more diagnostic requisition forms may be placed in a bag; the bag may be shipped to a testing lab.

Alternatively or additionally, and with continued reference to FIG. 1, collection device may include blotting paper. As defined in the disclosure, "blotting paper" is paper that can be used for collection of biological materials. A non-limiting example of material that can be collected using blotting paper includes blood. An example of paper that can be used as blotting paper includes filter paper. Filter paper may be made from high purity cotton linters. As an example, to analyze for presence or absence of antibodies for the SARS-COV2 infection, a dried blood specimen is collected by applying drops of a human subject's blood onto the blotting paper. Blood may be drawn by lancet from a finger, heel, toe, or the like. Once blood dries on paper, it may be shipped to a lab with a diagnostic requisition form and/or a unique identifier for analysis.

Alternatively or additionally, and further referring to FIG. 1, collection device may include a sterile dry container. Dry container may include any closure device to close dry container. These may include, but are not limited to, threaded closures, stoppers, metal caps, and the like. Collection device may contain sputum. As an example, a human subject may expectorate a sample of sputum into a dry container; once collected, the dry container containing the sputum may be shipped to a lab with a diagnostic requisition form and/or a unique identifier for analysis.

Still referring to FIG. 1, specimen may also include a unique identifier on the collection carrier human subject. As defined in this disclosure, a "unique identifier" is any identifier that refers to only one human subject. A unique identifier may include a specific sequence of characters, numbers, letters, and/or words that may identify a particular human subject. A unique identifier may include a globally recognized uniform identifier such as a uniform code commission (UCC) barcode. A unique identifier may include an optically captured and/or an otherwise captured identifier from a near field communication (NFC) tag or a radio frequency identifier (RFID) tag. As an example, a barcode containing human subject descriptive data may be included in the disease agent sampling kit which is used to acquire the specimen. As defined in this specification, "human subject descriptive data" is defined as data that is unique to a particular human subject. Human subject descriptive data may include, but without limitation, a subject's name, contact information, ethnicity, number of people residing in the subject's household, and the like. Human subject descriptive data may further include, without limitation, the subject's symptoms, the subject's data of birth, any recent infections, any locations where the subject has travelled to, any known exposure to disease agents, medications, allergies, and the like.

Additionally or alternatively, and still referring to FIG. 1, human subject descriptive data may be collected from a human subject by the use of a web portal. As an example, and prior to sending a disease agent sampling kit, a medical facility may send the human subject a web link containing the universal resource locator (URL) address to the web portal used to collect the human subject descriptive data. Alternatively, a human subject may enter human subject descriptive data by using a computing device configured to receive the human subject descriptive data from the human subject. Computing device may use a machine-learning model and/or other automated process and/or program that receives responses from the human subject to questions and outputs iteratively further questions for the user to answer. For example, a selection of common medical conditions may be displayed to the human subject; the human subject may select conditions that are appropriate to that individual human subject.

Additionally or alternatively, and with further reference to FIG. 1, computing device may be capable of compliance with security requirements of the Health Insurance Portability and Accountability Act (HIPAA). As an example, two step authentications may be required. Two-step authentication may ensure that the human subject is identified property and to secure the information before the human subject sends human subject descriptive data or receives a response from the computing device. Other examples of security measures to protect the individual' data and privacy include, but are not limited to encryption of responses, requiring strong passwords, like 15-character passwords, or the like.

Additionally, or alternatively, and with continued reference to FIG. 1, human subject descriptive data may be stored in a laboratory information management system or LIMS. As used in this disclosure, a "laboratory information management system" is defined as a device that manages and stores data such as the human subject descriptive data, specimen information such as what disease agent to test, a human subject's test results, analytical methods used for clinical analysis, any instrumentation used for the clinical analysis, methods to validate results, and the like. A LIMS system may include a database, for instance as described in further detail below. The database may contain human subject information stored in tables because of entries made by the human subject. For example, the human subject's ethnicity may be stored in the ethnicity table; the human subject's email address may be stored in the contact information table. As an example, once a human subject enters human subject descriptive data through a web portal application, the data may be stored in a secondary database until sample is ready for testing. Once a specimen and/or sample is ready for testing, human subject descriptive data may be transferred to the database in LIMS system. A unique identifier, such as a barcode, may match human subject's human subject descriptive data to a specimen.

Still referring to FIG. 1, at step 110, method may retrieve by the computing device human subject descriptive data as a function of the unique identifier. Human subject descriptive data collected from the human subject may be used to generate a human subject profile and used to generate the unique identifier such as, but not limited to a barcode. An input device may be used to acquire the unique identifier. A non-liming example of an input device may include an optical scanning device. An "optical scanning device," as defined in this disclosure, is a computing device that uses light, which may include actively generate and/or ambient light, to scan codes, text, or graphical images. An optical scanning device may be implemented as hardware or software. Examples of input optical scanning devices include, but are not limited to, a barcode reader, an image scanner, a light pen, a camera, or the like. Other input devices would depend on the type of unique identifier generated. For example, an RFID reader may be used to read an RFID tag when a unique identifier is an RFID tag. As the unique identifier may include and/or be associated with human subject descriptive data which is stored in a database, once the specimen arrives in the laboratory, the identifier may be scanned using an input device to match the human subject descriptive data in the database with the human subject descriptive data associated with the unique identifier. Specimen may be tracked throughout the specimen's lifecycle in the laboratory.

Still referring to FIG. 1, at step 115, computing device generates an identity for a second disease agent. Generating the disease agent includes generating a classifier using a first machine-learning process as a function of human subject descriptive training data, wherein the human subject descriptive data correlates human subject descriptive data with a second disease agent.

Figure 2:
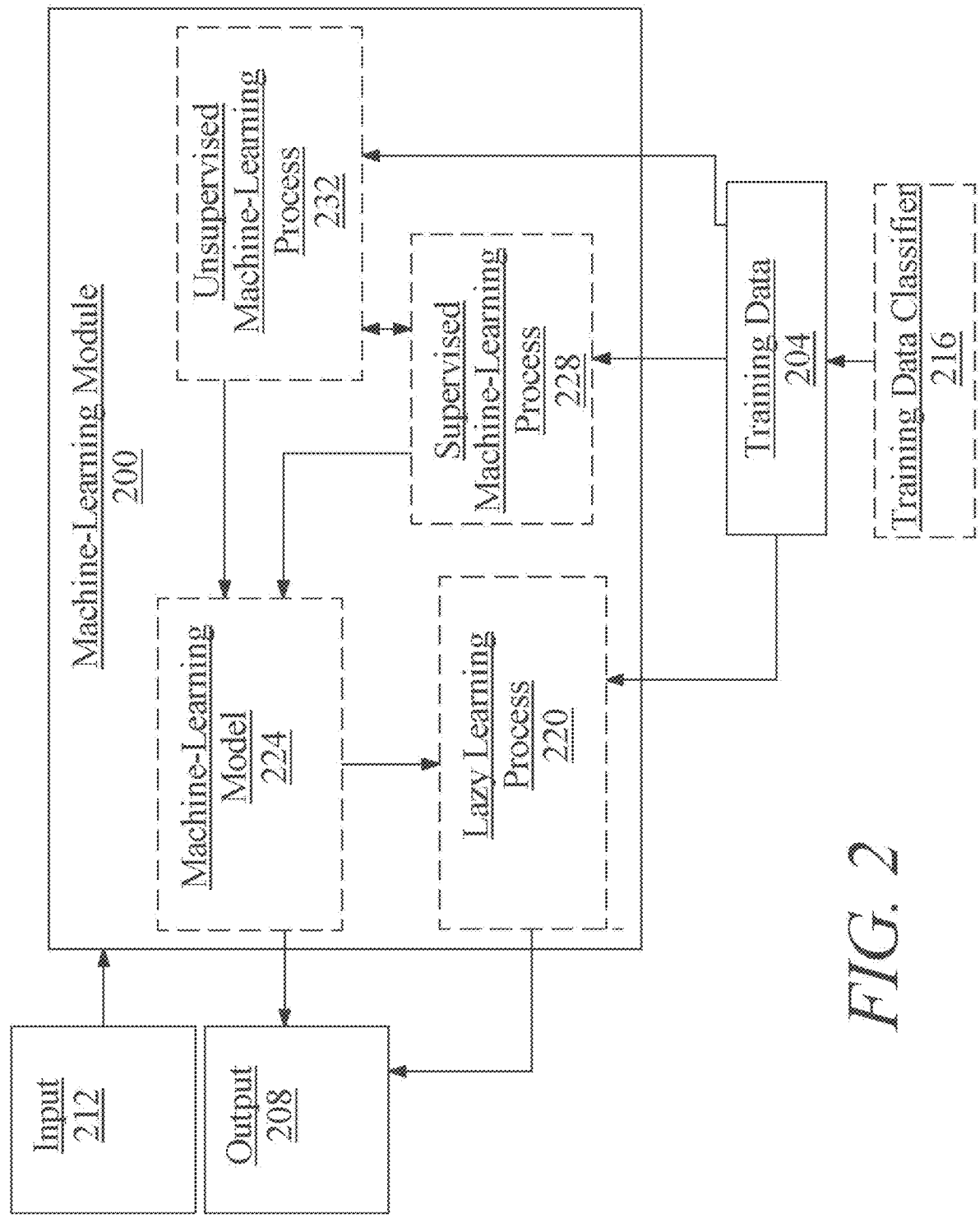
FIG. 2 is a block diagram of an exemplary embodiment of a machine-learning module.

Referring now to FIG. 2, an exemplary embodiment of a machine-learning module 200 that may perform one or more machine-learning processes as described in this disclosure is illustrated. Machine-learning module may include any suitable Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm that will be performed by a computing device/module to produce outputs 208 given data provided as inputs 212; this is in contrast to a non-machine learning software program where the commands to be executed are determined in advance by a user and written in a programming language.

Still referring to FIG. 2, "training data," as used herein, is data containing correlations that a machine-learning process may use to model relationships between two or more categories of data elements. For instance, and without limitation, training data 204 may include a plurality of data entries, each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail below. Training data 204 used by machine-learning module 200 may correlate any input data as described in this disclosure to any output data as described in this disclosure. As a non-limiting illustrative example, the machine learning model may receive human subject descriptive data as inputs and outputs a second disease agent.

Further referring to FIG. 2, training data may be filtered, sorted, and/or selected using one or more supervised and/or unsupervised machine-learning processes and/or models as described in further detail below; such models may include without limitation a training data classifier 216. Training data classifier 216 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 200 may generate a classifier using a classification algorithm, defined as a process whereby a computing device and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify elements of training data to persons infected with a disease agent, for example SARS-CoV-2 residing in a particular county or zip code.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 2, machine-learning processes as described in this disclosure may be used to generate machine-learning model 224. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 228.

At least a supervised machine-learning process 228, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include human subject descriptive data as described above as inputs, a disease agent identities as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

Further referring to FIG. 2, machine learning processes may include at least an unsupervised machine-learning processes 232. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 2, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data 204.

Referring again to FIG. 1, computing device may generate identity of the second disease agent as a function of descriptive data and classifier. Computing device may output a second disease agent that is identical to first disease agent and/or a second disease agent that is distinct from the first disease agent. A positive result for a first disease agent may result when an identity of the second disease agent is identical to the identity of the first disease agent and there is a positive result for the presence of the second disease agent.

With continued reference to FIG. 1, at step 120, method may extract a sequence of genetic material from the specimen using an automatic robot. The use of the automatic robot allows for high throughput testing. As defined in this disclosure, "high throughput" testing is the analysis of samples in a faster manner which allows for a testing and processing of more samples in less time. Extraction of sequence of genetic material includes a liquid extraction. High throughput may be achieved by working faster, analyzing multiple samples at once, or simultaneously handling multiple aspects of a sample at the same time. For liquid extraction, an automated robot may be used. Use of an automated robot may allow for dispensing precise amounts of specimen, reagents, or any other liquids to, for example, a well plate or a sample container. An example of an automatic robot used for preparation of liquid extraction may include the i-Pipette series by Apricot Designs™. Use of an automatic robot may provide for preparation and processing of between about 1,000 and about 10,000 samples per day, between about 1000 and about 7,000 samples per day, and/or between about 1,000 and about 3000 samples per day. Use of an automatic robot may provide for preparation and processing of between about 96 to about 1536 samples per hour; between about 96 to about 384 samples per hour; or between about 96 to about 192 samples per hour, In an embodiment, an automatic robot may process about 384 samples per hour. In another embodiment, automatic robot may process about 1536 samples per hour. A 3D printed plate with a capacity of 384 wells may be used to perform extraction. Commercial 384 well plates such as a Web Seal+384 Non Coated Plastic Microplate (Thermo Fisher Scientific) may be used. Well plates of other capacities such as, but not limited to, well plates having 96, 192, 1536, 3456, 6144 wells may be used.

Additionally, and still referring to FIG. 1, a Reverse Transcription-Polymerase Chain Reaction method may be used for the extraction (RT-PCR). (See, for example, *The CDC 2019—Novel Coronavirus (2019-nCoV) Real Time RT-PCR Diagnostic Panel*, released June 2020). One of ordinary skill, upon reviewing the entirety of this disclosure, will understand that this method may be utilized to convert an RNA sample to complementary DNA (cDNA) to provide a DNA template. One of ordinary skill, upon reviewing the entirety of this disclosure would understand that RT-PCR reagents are readily available from commercial vendors.

Alternatively or additionally, extraction may be sequenced by use of direct high-throughput sequencing using a microbial-specific database. As a non-limiting example, a PMSeq® clinical database (BGI) may be used to compare extraction to a species information of suspected disease agentic microorganisms and provide information about a potential infection. Database may divide detection process into a DNA detection process and an RNA detection process where the DNA detection process is used primarily for the detection of disease agents involving bacteria or fungi, proviruses, or the like. RNA detection process may be used for the detection of disease agents derived from RNA viruses. Sequencing may include analysis using other databases. Databases include, but are not limited to, a human genome database, such as, but not limited to the Genome Database; a disease agent genome database such as GeneDb; and a medical interpretation algorithm such as ChimeraSlayer, CATCh, or the like.

Still referring to FIG. 1, computing device may aggregate a plurality of human subject specimens into a single extraction. As defined in this disclosure, biological samples may be "pooled" when individual specimens are combined in, for example, one well of the well plate. An advantage of pooling specimen may be to use less reagents when running the analysis. The pooled samples may include specimens from the same human subject. The pooled samples may include samples from a plurality of human subjects. Another advantage is that it increases the efficiency and the throughput of the lab. A lab may pool between 2 and 10 specimens; between 2 and 8 specimens; or between 2 and 5 specimens. The specimens may be pooled according to a disease agent of interest. As a non-limiting example, 5 specimens potentially infected with SARS-CoV-2 may be pooled together into a single well. Specimens may be pooled by a descriptive human subject data. For example, several specimens may be pooled by zip code and tested for a variety of disease agents. A person of ordinary skill, having the benefit of the entirety of this disclosure, will be able to determine other methods of pooling specimens to test.

Still referring to FIG. 1, at step 125, computing device may determine a test result for the first disease agent as a function of the sequence of generic material. A test result may be positive, negative, inconclusive, false positive or false negative. A positive test result, as defined by this disclosure is a test result where the disease agent or plurality of disease agents being tested are found in the specimen. For example, a positive test for SARS-CoV-2 may indicate that the genetic material extracted indicates a positive infection for SARS-CoV-2. In an embodiment, the test result is a positive result. A positive result may be obtained based on achieving a certain criterion established for a particular analysis. For example, a specimen is considered positive for 2019-nCoV if 2019-nCoV marker (N1, N2) cycle threshold growth curves cross the threshold line within 40.00 cycles (<40.00 Ct). Each individual disease agent test has an established criterion for a positive result.

Alternatively or additionally, with continued reference to FIG. 1 test result may include a negative test result, defined by this disclosure as a test result where the disease agent or plurality of disease agents being tested are not found in the specimen. For example, a negative test for SARS-CoV-2 may indicate that the genetic material extracted indicates a negative infection for SARS-CoV-2. As an non-limiting example, a specimen may considered negative for SARS-CoV-2 if all 2019-nCoV marker (N1, N2) cycle threshold growth curves do not cross a threshold line within 40.00 cycles (<40.00 Ct) and an RNase P growth curve DOES cross the threshold line within 40.00 cycles (<40.00 Ct). Each individual disease agent test may have an established criterion for a positive result.

Alternatively or additionally, with continued reference to FIG. 1, an inconclusive test result, as defined by this disclosure is a test result where a disease agent or plurality of disease agents being tested are not clearly positive or negative. In an embodiment, test result may be inconclusive. For example, an inconclusive test result obtained for a specimen tested for SARS-CoV-2 antibodies may be due to not enough antibodies present in, for example, blood analyzed. It may not be clear if a level of antibodies would be high enough to indicate an infection.

Alternatively or additionally, with reference to FIG. 1, a test result may include a false positive. A false positive test result, as defined by this disclosure is a test result that shows an infection by a disease agent or plurality of disease agents when, for example, a control sample or a specimen should show a negative result. For example, while running a negative control sample, in which a negative result for a disease agent is expected, a positive result may be obtained instead.

Alternatively or additionally, still referring to FIG. 1, a false negative test result, as defined by this disclosure is a test result that does not shows an infection by a disease agent or plurality of disease agents when, for example, a control sample or an specimen actually should show a positive result. For example, while running a negative control sample, in which a negative result for a disease agent is expected, a positive result is obtained instead.

Still referring to FIG. 1, method may establish communications that includes an authorized human subject contact as a function of a positive result. As defined in this disclosure, an "authorized human contact" is a person or plurality of person which are designated by the human subject to receive test results. An authorized contact may be an immediate family member such as, but not limited to, the human subject's mother, father, siblings, a spouse, grandparents, the human subject's children, and the human subject's in laws. An authorized contact may be a friend, any religious leader such as a priest, a Rabbi, or an Imam. An authorized contact may be a person or plurality of persons that may have had prior contact with the human subject that may have been potentially infected by a disease agent. An authorized contact may be a government official or agency responsible for the management of the public health system where the human subject potentially infected by a disease agent resides. An authorized contact may be a school principal, a school superintendent or college dean when, for example, the human subject is a student. An authorized human subject contact may be an expert such as, but not limited to a doctor, nurse, nurse practitioner, epidemiologists, and the like.

Alternatively or additionally, still referring to FIG. 1, computing device may initiate a conferencing event with the authorized contact. A conferencing event may be a video conference, a telephone conversation, a text conversation, and the like. A "telehealth conferencing event," as defined in this disclosure, is a conferencing event arranged to discuss health-related issues. Conferencing event may take place between one or a plurality of authorized contacts. For example, after a positive result for a disease agent, a doctor and the human subject's spouse may engage in a telehealth to discuss a potential isolation plan for residents in the same household as the human subject with a potential infection for a disease agent.

Alternatively or additionally, and with continued reference to FIG. 1, computing device may determine a presence of the first and second disease agent in the specimen based on a comparison of the identity of the first and second disease agent. For example, the classifier that receives human subject descriptive data as an input and outputs a second disease agent may output a second disease agent that is identical to the first disease agent. A positive result for a second disease agent would result when the identity of the second disease agent is identical to the identity of the first disease agent and there is a positive result for the presence of the first disease agent.

Still referring to FIG. 1, computing device may perform an textual conversation with a user, the textual conversation including transmitting to a computing device, a plurality of potential user symptoms and receiving a user selection of a potential user symptom from the plurality of user symptoms. A "textual conversation," as defined in this disclosure, is a conversation involving either text or messaging that is interactive. Inputs and/or outputs may be exchanged iteratively using, for example, messaging services and/or protocols, including without limitation any instant messaging protocols. Based on inputs received from user, system may determine what the potential symptoms are. Persons skilled in the art, upon reviewing the entirety of this disclosure, will be aware of a multiplicity of communication protocols that may be employed to exchange text messages as described herein. Text messages may be provided in textual form and/or as audio files using, without limitation, speech-to-text and/or text-to-speech algorithms.

Alternatively or additionally, with continued reference to FIG. 1, a textual conversation may include one or more image files. Image file formats include, but not limited to, Joint Photographic Experts Group (JPEG), Portable Network Graphics (PNG), Graphics Interchange Format (GIF), Tagged Image File (TIF), Portable Document Format (PDF), Encapsulated Postscript (EPS), Raw Image Files (RAW), or the like. A user may capture an image using a device using a computing device. Devices may include, without limitation a mobile camera, a scanner, a digital camera, a tablet computer, or the like. For example, a human subject may take a picture of a certain area of their body and include the picture in the textual conversation.

Alternatively or additionally, with reference to FIG. 1, a user may initiate a textual conversation by using a text messaging protocol; Text messaging may include instant messaging protocol, such as, but not limited to Bitmessage, Bonjour, Matrix, short message service (SMS), or the like. Text messages can be classified in different categories depending on the subject of the message by processing the messages using, for example, natural language processing. Text messages and/or textual communication may include, without limitation, messages displayed and/or received using audio input and/or output devices, including using text-to-speech and/or speech-to-text technology.

Still referring to FIG. 1, computing device may generate a recommendation for the human subject, wherein the second disease agent has a different identity from the first disease agent in the analyzed extracted sequence of generic material. For example, classifier may output a second disease agent that is different to the first disease agent. An identity of second disease agent may not match an identity of first disease agent. As defined in this disclosure, a "recommendation" may include one or a plurality of treatment care instructions based on an identity of the second disease agent. Recommendations may be identical to recommendations given for first disease agents. Recommendations may be based on input of symptoms from human subject. Recommendations may not correspond to a medical recommendation. For example, a non-medical recommendation may be to "isolate" or to "drink more fluids. A medical recommendation, for example, may instruct a human subject to "take a pain reliever" or to "schedule an appointment with a health professional." Negative results for a first disease agent may be compared against a plurality of symptoms stored in a symptoms table in a database. Another liquid extraction to test for a different disease agent may result.

Still referring to FIG. 1, computing device may determine a human subject contact profile. As defined in this disclosure, a "human subject contact profile" is a profile that includes human subject data describing information that may be used to generate contact tracing information. Data may include, but not limited to, places where human subject has travelled to, their home address, number of people that live in the human subject home, the name of the people that live in the human subject's home, the work address of the human subject, name of immediate supervisor, and the like. Determining the human subject contact profile may include prompting a human subject for intake data and receiving human subject intake data as a function of the prompting for intake data. Intake data may have the same form and content as human subject descriptive data. Determining the human subject contact profile may include generating a second machine-learning process as a function of contact training data. The contact training data may correlate intake data elements with a human subject contact profile elements. The human subject contact profile is determined as a function of the human subject intake data and the second machine-learning process. The machine-learning process is as described above.

Figure 3:
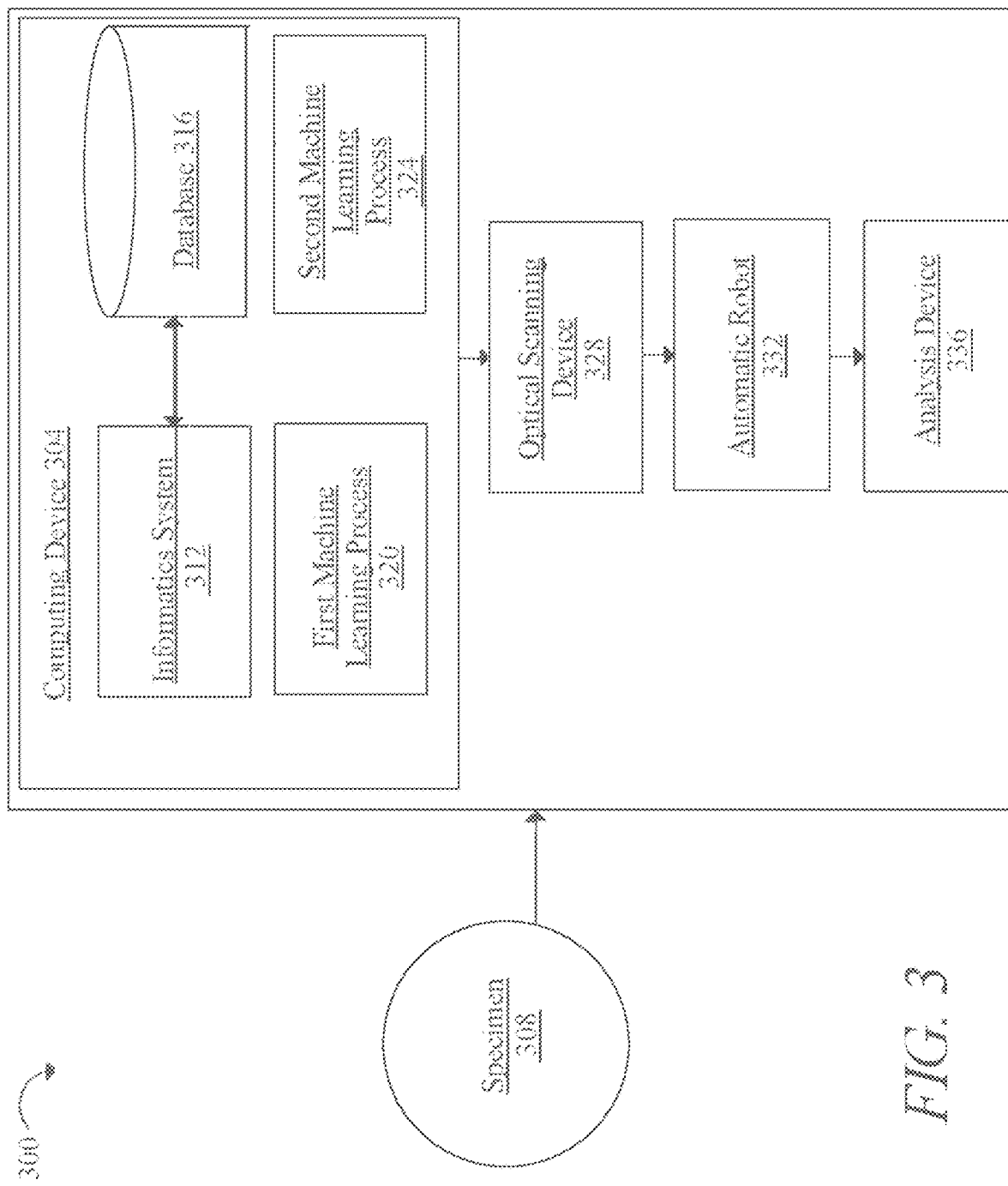
FIG. 3 is a block diagram of an exemplary embodiment of an automated biological sample testing system.

Referring now to FIG. 3, an exemplary embodiment of a system 300 for a system for automated viral analysis is described. System 300 may include computing device 304 configured to manage specimen 308 collected from a human subject with a potential infection of a first disease agent. In an embodiment, the first disease agent may be a coronavirus. Computing device may include any computing device as described in this disclosure, including without limitation a microcontroller, microprocessor, digital signal processor (DSP) and/or system on a chip (SoC) as described in this disclosure. Computing device 304 may include, be included in, and/or communicate with a mobile device such as a mobile telephone or smartphone. Computing device 304 may include a single computing device 304 operating independently, or may include two or more computing device 304 operating in concert, in parallel, sequentially or the like; two or more computing device 304 may be included together in a single computing device 304 or in two or more computing device 304. Computing device 304 may interface or communicate with one or more additional devices as described below in further detail via a network interface device. Network interface device may be utilized for connecting computing device 304 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing device, and any combinations thereof. A network may employ a wired and/or a wireless mode of communication. In general, any network topology may be used. Information (e.g., data, software etc.) may be communicated to and/or from a computer and/or a server. Computing device 304 may include but is not limited to, for example, a server or cluster of computing devices in a first location and a second computing device or cluster of computing devices in a second location. Computing device 304 may include one or more computing devices dedicated to data storage, security, distribution of traffic for load balancing, and the like. Computing device 304 may distribute one or more computing tasks as described below across a plurality of computing devices of computing device 304, which may operate in parallel, in series, redundantly, or in any other manner used for distribution of tasks or memory between computing devices. Computing device 304 may be implemented using a "shared nothing" architecture in which data is cached at the worker, in an embodiment, this may enable scalability of system 300 and/or computing device 304.

Continuing to refer to FIG. 3, computing device 304 and/or any module thereof may be designed and/or configured to perform any method, method step, or sequence of method steps in any embodiment described in this disclosure, in any order and with any degree of repetition. Furthermore, modules as described in this disclosure are provided for exemplary purposes to provide the functional and structural processes and/or configurations that may be used to perform processes and instantiated, whether in the form of hardware circuitry, process-based software code, machine-language, object oriented language, or programming or any other implementation that any person skill in the art, having the benefit of this disclosure may use to implement process and/or configuration as described herein; modules as described in this disclosure need not be implemented as separate modules. For instance, computing device 304 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 304 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Alternatively or additionally, and still referring to FIG. 3, computing device 304 may include an informatics system 312. As used in this specification, a "informatics system" is a tool for laboratory and data management which includes, but not limited to, workflow management, specimen tracking, process management, and the like. A non-limiting example of informatics system 312, include a laboratory information management system (LIMS).

Additionally or alternatively, and referring to FIG. 3, informatics system 312 may further connect to and/or include a database 316. Database 316 may be implemented, without limitation, as a relational database 316, a key-value retrieval database 316 such as a NOSQL database 316, or any other format or structure for use as a database 316 that a person skilled in the art would recognize as suitable upon review of the entirety of this disclosure. Database 316 may alternatively or additionally be implemented using a distributed data storage protocol and/or data structure, such as a distributed hash table or the like. Database 316 may include a plurality of data entries and/or records as described above. Data entries in a database 316 may be flagged with or linked to one or more additional elements of information, which may be reflected in data entry cells and/or in linked tables such as tables related by one or more indices in a relational database 316. Persons skilled in the art, upon reviewing the entirety of this disclosure, will be aware of various ways in which data entries in a database 316 may store, retrieve, organize, and/or reflect data and/or records as used herein, as well as categories and/or populations of data consistently with this disclosure. In some embodiments, network data, or other information such as user information, courier information, and alimentary provider information, may be stored in and/or retrieved from database 316.

Figure 4:
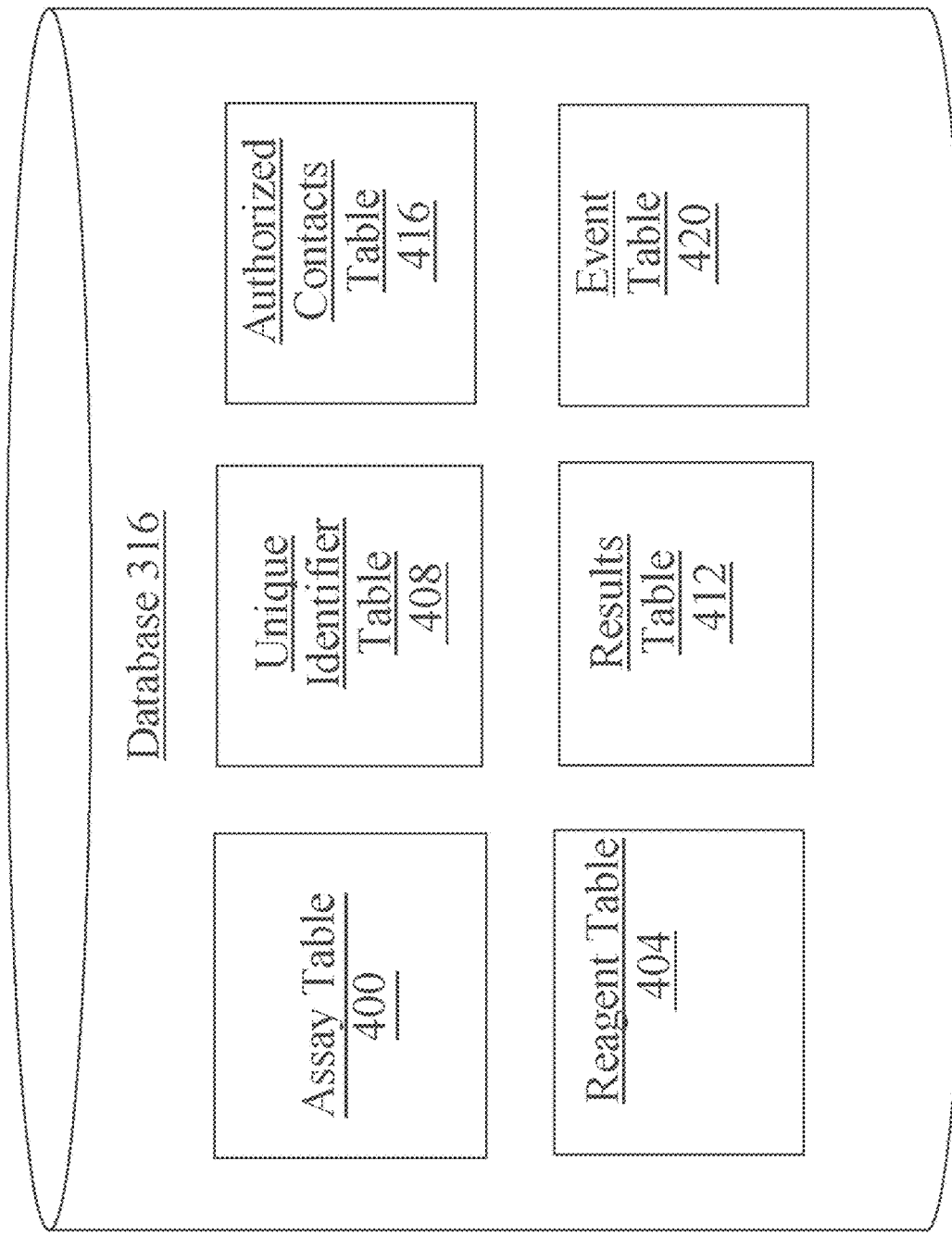
FIG. 4 is a block diagram of an exemplary embodiment of a database.

Referring now to FIG. 4 an exemplary embodiment of a database 316 is illustrated. Database 316 may, as a non-limiting example, organize data stored in the database according to one or more database tables. One or more database tables may be linked to one another by, for instance, common column values. For instance, a common column between two tables of database 316 may include an identifier of a human subject, such as a unique identifier or the like, for instance as defined below; as a result, a query may be able to retrieve all rows from any table pertaining to a given human subject's specimen or previous specimens. Other columns may include any other category usable for organization or subdivision of data, including types of data, common pathways between, for example, a human subject's contacts and any previous infection of any of those contacts, other previous infections by the human subject, or the like; persons skilled in the art, upon reviewing the entirety of this disclosure, will be aware of various ways in which expert data from one or more tables may be linked and/or related to expert data in one or more other tables.

Still referring to FIG. 4, one or more database tables in database 316 may include, as a non-limiting example, an assay table 400, which may be used to store biological assays which may be used in testing a specimen. This may include, but not limited to, a particular virus assay such as Influenza or SARS-CoV-2, a bacterial assay such as Botulism. or the like. As another non-limiting example, one or more tables in database 316 may include a reagent table 404 which may be used to store inventory information as to what reagents are used for a particular assay. As another non-limiting example, one or more tables in database 316 may include a unique identifier table 408. A unique identifier table 408 may include, but not limited to unique identifier information that may associate a unique identifier to the specimen of a human subject. As another non-limiting example, one or more tables in database 316 may include a results table 412. A results table 412 may include results regarding a specimen, or the like. As another non-limiting example, one or more tables in database 316 may include an authorized contact table 416. An authorized contact table 416 may include, but not limited to, the list of authorized contact information which may include names and contact information of authorized contacts to receive specimen results, preferred method of contact, or the like. As another non-limiting example, one or more tables in database 316 may include an event table 420. An event table 420 may contain events related to the lifecycle of a specimen from the moment the specimen is received in the lab to the time a result is obtained. For example, events may include "on hold," testing in process," "testing completed," or the like.

Figure 5:
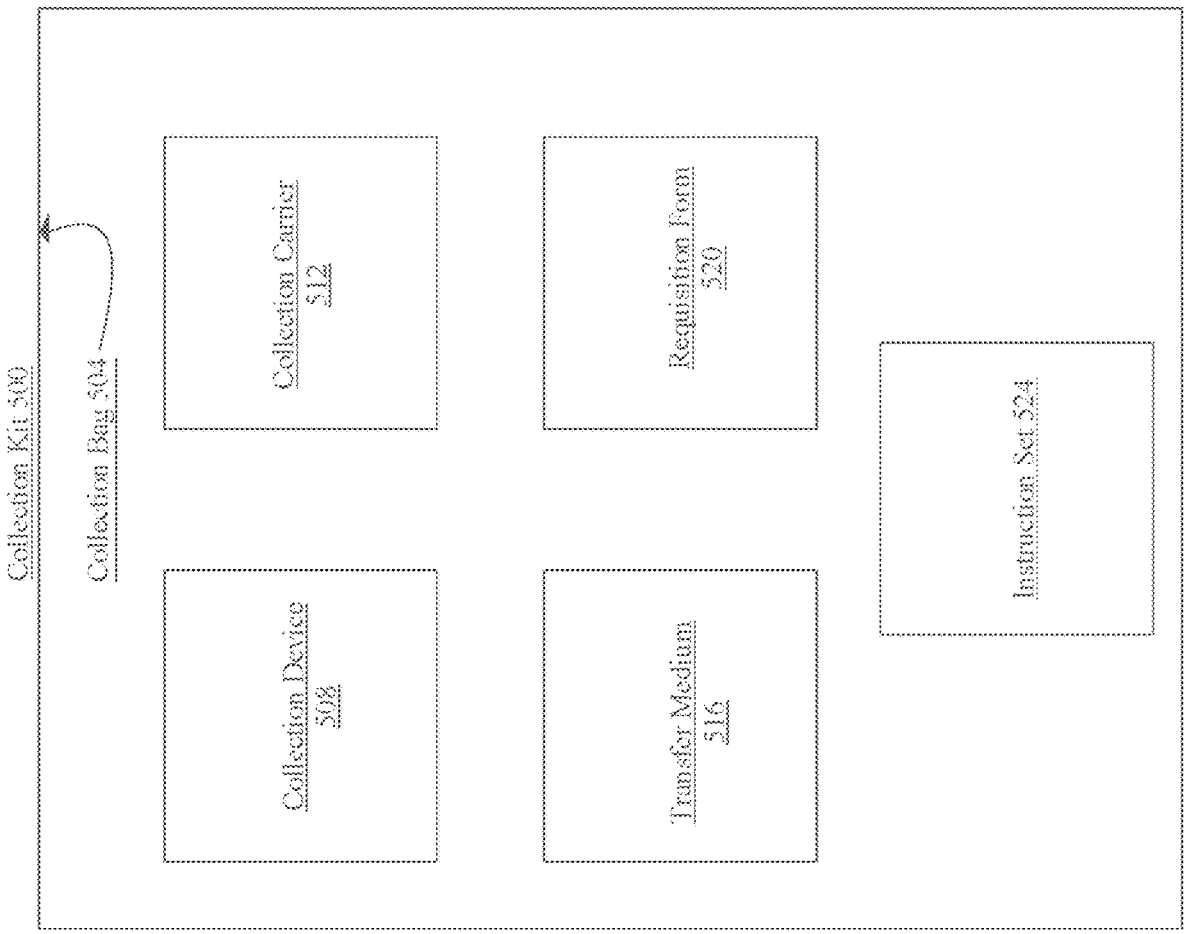
FIG. 5. is a block diagram of an exemplary embodiment of a collection kit.

Now referring to FIG. 5, the content of collection kit 500 that may be used to collect a specimen is described. The contents of a collection kit are included in a biohazard collection bag 504. The collection bag 504 may be of any color. The collection bag 504 may be made out of polypropylene, high density polyethylene, polyethylene, or the like. The collection bag 504 may be self-sealing; may seal using an airtight pressure closure, or the like. The collection bag 504 may be of any size, such as a 6"×9" bag. The collection bag 5504 may include a collection device 508. A collection device 508 may include a swab, blotting paper, or the like. Collection bag 504 may also include a collection carrier 512. In an embodiment, the specimen includes genetic material collected from the human subject using a collection device 508 and stored in collection carrier 512. In an embodiment, collection device 508 may include a swab and a transfer medium where the swab is dipped in the transfer medium. Collection carrier 512 may include a sterile vessel can be a glass vial with a stopper, a plastic urine sample cup, a test tube, or the like. A typical volume of a collection carrier 512 may be, but not limited to, 90 mL.

Alternatively or additionally, and still referring to FIG. 5, collection bag 504 may include a vial containing a transfer medium 516. Transfer media has been described and may be implemented without limitation as discussed above in FIGS. 1-4. In another embodiment, collection device 5508 may include a swab and a transfer medium where the swab is dipped in the transfer medium. In another embodiment, collection device 508 may be blotting paper. Collection device 508 have been described above and may be implemented without limitation as described in FIGS. 1-4.

Alternatively, or additionally, and still referring to FIG. 5, collection kit 500 may include a requisition form 520. Requisition form 516 may include information from the human subject about the specimen. For example, requisition form 516 may include, but not limited to, information regarding the type of analysis or plurality of analyses requested, a description of the specimen, the name of the person requesting the analysis, and the like. Collection bag 504 may include instruction set 524 on how to conduct the acquisition of the specimen. As a non-limiting example, instructions on how to acquire a sample from the nasopharynx region may be included. Instruction set 524 may be written in a foreign language. For example instruction set 520 included in collection kit 500 may be written is Spanish, Chinese-Mandarin, Chinese-Cantonese, Japanese, Vietnamese, French, Italian, and the like.

Alternatively or additionally, and still referring to FIG. 5, collection kit 500 may include a unique identifier 528. Unique identifier 528 has been described and may be implemented without limitation as described in FIGS. 1-4. In an embodiment, the specimen includes a unique identifier 528 on collection carrier 512. The unique identifier may contain human subject descriptive data. For example, collection kit 500 may contain a barcode. The barcode would associate a specimen with a human subject. The barcode would be used to track the sample through the lifecycle of the sample.

Referring now to FIGS. 6A-6L, computing device 304 may be configured to retrieve human subject descriptive data. Computing device 304 may be configured to identify human subject descriptive data as a function of the unique identifier. Computing device 304 may collect information that may include, but is not limited to, personal information about a human subject; medical history; demographic information; information about the human subject's household; or the like. Computing device 304 may be configured to be HIPAA-compliant. For example, computing device 304 may be configured to require two-step authentication. Another non-limiting example, computing device 304 may be configured to require communication. In an embodiment, computing device 304 may be used to create a human subject contact profile. Determining the human subject contact profile may include prompting a human subject for human subject descriptive data. Intake data may have the same form and content as human subject descriptive data. In an embodiment, computing device 304 may be configured to determine the human subject contact profile. The human subject contact profile may be generated by prompting a human subject for human subject intake data and receiving human subject intake data as a function of the prompting. Computing device 304 may by generate a second machine learning process 324 as a function of contact training data. The contact training data correlates intake data elements with a human subject contact profile. The human subject contact profile may be determined as a function of the intake data and the second machine-learning process 324.

Additionally or alternatively, and still referring to FIGS. 6A-6L. computing device 304 may be configured to collect human subject descriptive data using web portal 600. Computing device 304 may be configured to run in a foreign language. For example, computing device 304 may present instructions and accept responses in Spanish, Chinese-Mandarin, Chinese-Cantonese, Japanese, French, Italian, German, and the like. As an example, webportal 600 may ask a human subject a series of questions where the human subject would be the subject of a SARS-CoV-2 test. Human subject descriptive data may be the same as human subject intake data. FIGS. 6A-L shows an exemplary embodiment of the information that may be collected using webportal 600.

Figures 6A, 6B:

FIG. 6A shows the initial screen that a human subject may see upon entering webportal 600. FIG. 6B shows a screen that may introduce the user to the process of human subject acquisition. Initially, a human subject may provide consent to use the data collected. The human subject may be advised that they will answer questions to establish commonalties and difference among the population of human subjects. The human subject may be reminded that they need to enter the unique identifier 528 in webportal 600. The human subject may be reminded that they will receive the results of the testing in a report.

Figure 6C:

FIG. 6C may prompt the human subject to enter their height and weight. This window may be for the user to enter the data as, for example, a free text. The window may also be configured for the user to move a marker in a graph to the appropriate response.

Figure 6D:
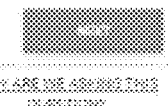

FIG. 6D shows where a human subject webportal 600 may select their blood group. This entry may be made, for example, from a drop-down menu, a free text field for the human subject to enter the appropriate blood group, or the like. The human subject may be prompted to select their ethnicity. This entry may be made, for example, from a drop-down menu, a free text field where the human subject may enter the appropriate ethnicity. For example, a human subject may select or enter "white" as their ethnicity. Other selection that a human subject may select or enter include, but not limited to "Black or African American," "American Indian or Alaska Native," "Asian," "Native Hawaiian and Other Pacific Islander," and the like.

Figure 6E:
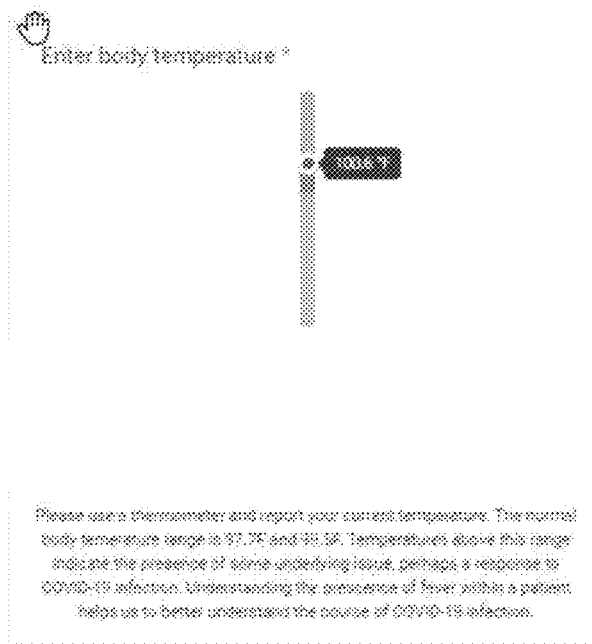

FIG. 6E may ask the human subject to enter their body temperature. The human subject may be presented, for example, with a slider where they can choose their approximate body temperature. Another non-limiting example may present the user with a blank form for the user to enter the value of their body temperature.

Figure 6F:
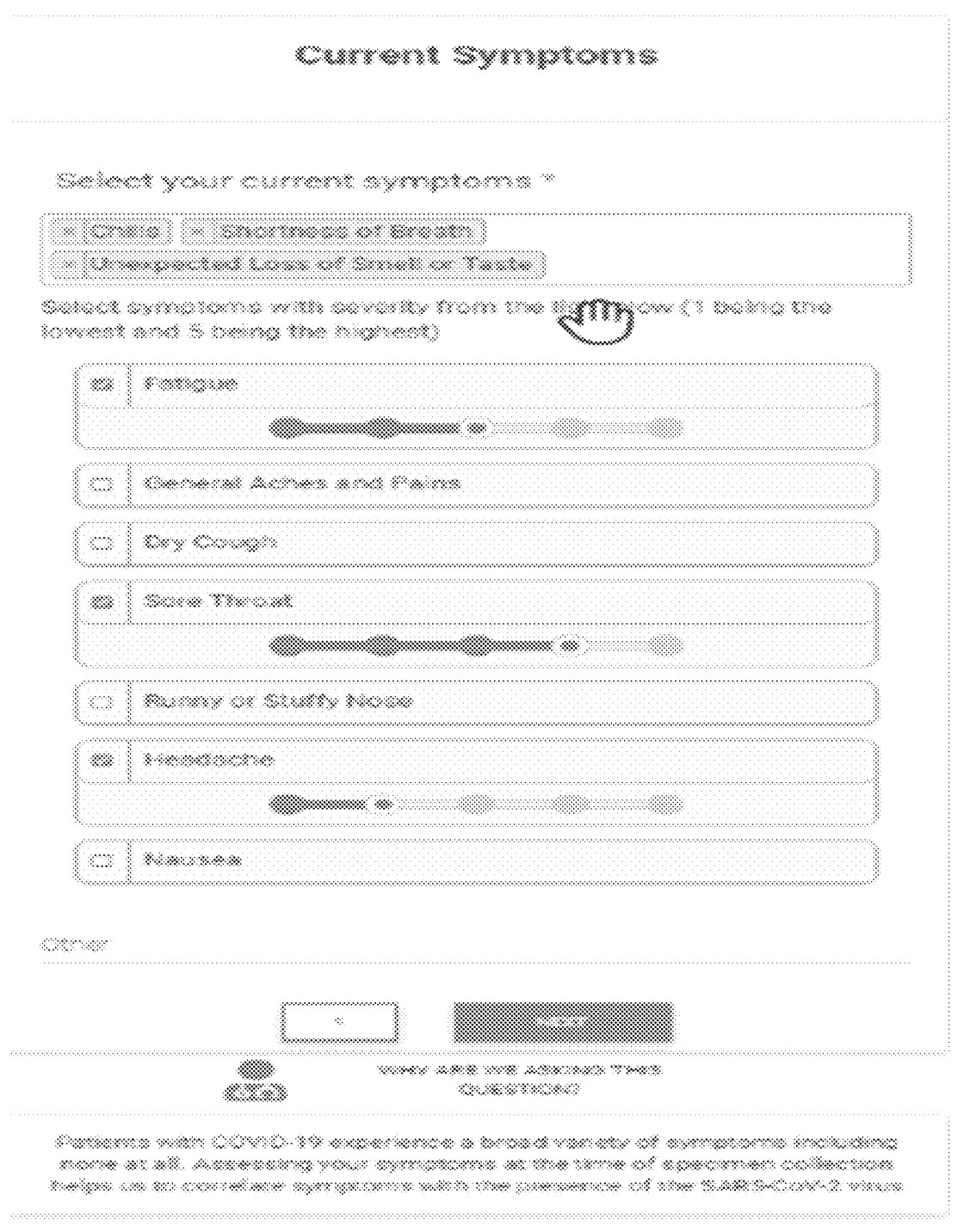

FIG. 6F may allow the human subject to enter their symptoms and the severity of the symptoms. As a non-limiting example, the human subject may select "Nausea" as one of their symptoms. The human subject may select the severity of the symptom, in this case nausea, by selecting from a range between 1 and 5 where 1 is the lowest meaning a mild symptom to a 5 which would may indicate that the symptom is severe. The window may be configured for the human subject to click on a symptom. The window may be configured as a free text window where the human subject enters their symptoms as text in the window.

Figure 6G:
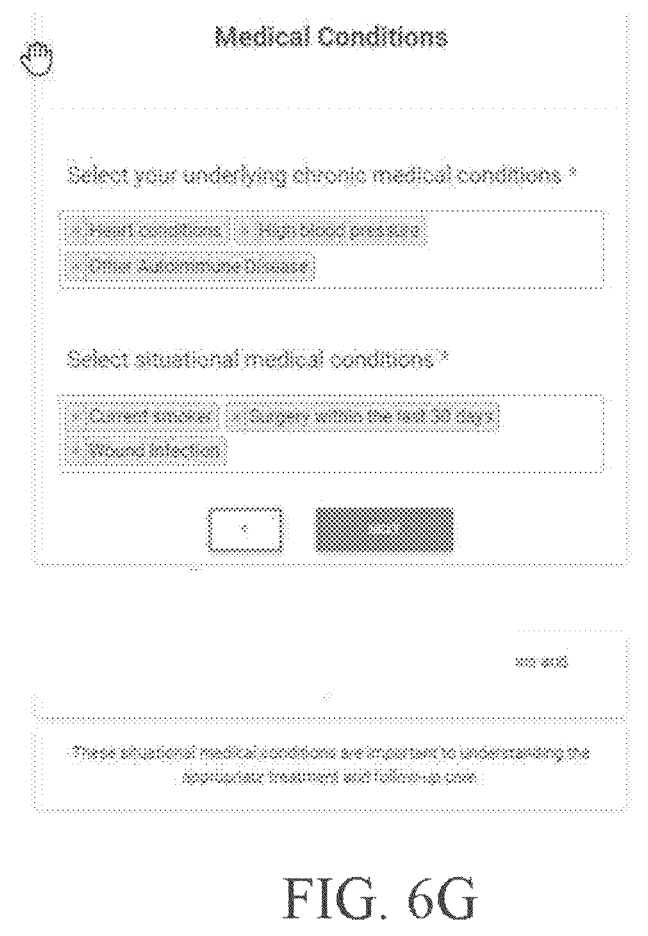

FIG. 6G may allow the user to enter any underlying or pre-existing condition. For example, a human subject may select "Diabetic" and/or "High Blood Pressure." The human subject may, but not limited to, select their pre-existing conditions. The human subject may enter their pre-existing conditions as free text.

Figure 6H:
Figures 6I, 6J:

FIG. 6H may ask the human subject to enter the number of people living in the same household as the human subject. The window may group the number of people living in a household by age range. For example, the window may ask the human subject the number of people with age range 0-19 living in the same household. The human subject may enter the number of people residing in the same household as the human subject of age ranging from 20-39, of age ranging from 40-59, of age 60 or higher, or the like. The window may be configured for the human subject to enter the value for an age range of people residing in a household as free text. The window may also be configured for the human subject to select a value from a drop-down menu, or the like. In FIG. 6H, the human subject may enter the number of pets residing in the same household as the human subject. For example, a human subject may select from a drop-down menu the number of pets in their household. The window may also be configured to accept a numerical value for the number of pets as a free-text. FIG. 6I may allow a human subject to enter a value for the number of people the human subject may have talked to that were not wearing a mask. For example, the window may be configured to allow the human subject to enter a numerical value as an answer. The window may be configured to allow, for example, the human subject to select the answer from a drop-down menu. In FIG. 6I, the human subject may be asked to enter their exposure to another person with, for example, SARS-CoV-2. The human subject may select the answer from a drop down menu containing various numerical values. The window may be configured, for example, to allow the user to enter a numerical value as free text.

In FIG. 6I, the human subject may be asked to describe their work setting. For example, a human subject may respond with an answer that the human subject works in a healthcare environment. The human subject may select an answer from a drop down menu of choice, enter the answer as free text or the like.

In FIG. 6J, the user is prompted to enter the medications or over-the-counter drugs that the human subject is taking. For example, a human subject may start entering a medication, and the window may offer the human subject a choice of medications containing the same root that the user entered where the user then makes a selection. The window may be configured to allow the user to enter the entire name of the medication as free text.

Figures 6K, 6L:

In FIG. 6K, the human subject may enter the unique identifier 5524 into a window in webportal 600. For example, the human subject may enter a barcode that may be included in collection bag 504. The human subject may enter the value of the unique identifier in free-text form. In another non-limiting example, the human subject may begin typing the barcode where the web portal 600 may present the human subject with potential values for the barcode where the human subject can select their barcode. In another non-limiting example, webportal 600 may allow the user to use a mobile device equipped with a scanning device to take an image of the barcode and attach the image to the window. The human subject may be prompted to enter an image file in the window. The image file may be formatted as jpg, png. gif, .pdf, or the like. The window may be configured with a recorder option where the recorder option may allow the human subject to record using their voice the value of the barcode. In FIG. 6L, the human subject may receive an acknowledgement of the submission.

Referring again to FIG. 3, human subject descriptive data collection device 320 may include a conversational agent running on computing device 304. As defined in this disclosure, a "conversational agent" is any dialogue system that not only conducts natural language processing but also responds automatically using human language. The dialogue system may also read from (input channel) and respond with (output channel) speech, graphics, virtual gesture or haptic-assisted physical gestures. Non-limiting examples of a conversational agent include a chatbot, a voice artificial intelligent system, or the like. A conversation agent may include a human subject information response module configured to communicate interactively with a human subject device. The communication may be textual, by voice, or the like. The human subject information response module may transmit a plurality of human subject intake questions as described above to the human subject device where the human subject may respond. The human subject information response module may incorporate a machine-learning process and a classification algorithm to receive the human subject responses as inputs and outputs questions regarding additional human subject intake information.

Still referring to FIG. 3, computing device 304 may be configured to generate an identity of a second disease agent. Computing device 304 is configured to identify a second disease agent by generating a classifier using a first machine-learning process 320 as a function of human subject descriptive training data. The human subject training data correlates human subject descriptive data with a second disease agent. Computing device 304 may generate the identity of the second disease agent as a function of the descriptive data and the classifier. This may be implemented, without limitation, as described above in FIGS. 1-6.

Still referring to FIG. 3, in an embodiment the second disease agent may be identical to the first disease agent. This may be implemented, without limitation, as described above in FIGS. 1-6.

Still referring to FIG. 3, in an embodiment, computing device 304 may be configured to perform an encrypted textual conversation with the user, the textual conversation including transmitting to a computing device, a plurality of potential user symptoms and receiving a user selection of a potential user symptom from the plurality of user symptoms. This may be implemented, without limitation, as described above in FIGS. 1-6.

Still referring to FIG. 3, in an embodiment, computing device 304 may be configured to determine a presence of the first and second disease agent in the specimen based on a comparison of the identity of the first and second disease agent. This may be implemented, without limitation, as described above in FIGS. 1-6.

Still referring to FIG. 3, in an embodiment, computing device 304 may be configured to generate a recommendation for the human subject, wherein the second disease agent has a different identity from the first disease agent in the analyzed extracted sequence of generic material. This may be implemented, without limitation, as described above in FIGS. 1-6.

Still referring to FIG. 3, system 300 may include an optical scanning device 328 configured to configured to extract human subject descriptive data as a function of the unique identifier. An optical scanning device has been described above and may be implemented, without limitations, as described in FIGS. 1-6.

Still referring to FIG. 3, system 300 may include an automatic robot 332. Automatic robot 332 may be configured to extract a sequence of genetic material from the specimen. The automatic robot may be configured without limitation as described in FIGS. 1-6.

Still referring to FIG. 3, automatic robot 332 may aggregate a plurality of human subject specimens into a single extraction. This may be implemented, without limitation, as described above in FIGS. 1-6.

Still referring to FIG. 3, system 300 may include an analysis device 336. Analysis device 336 may determine a test result for the first disease agent as a function of the sequence of generic material. Analysis device 332 may amplify and quantitate DNA. For example, analysis device includes a quantitative Polymerase Chain Reaction (qPCR) instrument or a real time PCR instrument with thermal control. Examples of real time PCR instruments include the LightCycler96 (Catalog No. 05815916001, Roche) or Thermo Fisher Scientific QuanStudio 5 Series qPCR system with 384 well plate capacity (Catalog No. A28140). As PCR progress is monitored by fluorescence, the real time PCR instrument may include a fluorimeter. As an example, RNA is converted to complementary DNA by reverse transcription. The PCR reaction amplifies and detects the sequence of interest which uses fluorescence reporters as a real time detection mechanism. Following the amplification of complementary DNA after a number of cycles, a sequence of interest, for example, for a disease agent of interest may be measured. For example, after 45 PCR cycles, the human subject specimen may generate a complementary DNA sequence that shows the presence of the SARS-CoV-2 viral DNA. This may indicate a positive result for the presence of the virus. In an embodiment, the test result is a positive result. In another embodiment, communications with an authorized human subject contact may be established as a function of the positive test result. This may be implemented without limitation as described in FIGS. 1-6. In another embodiment, system 300 may initiate a conferencing event with the authorized contact. This may be implemented, without limitation, as described above in FIGS. 1-6.

With continued reference to FIG. 3, analysis device 336 may perform a serological test on a blood sample to detect the presence of antibodies for a disease agent. For example, the analysis may look for antibodies against a disease agent like the SARS-CoV-2 virus for infections that have occurred in the past. A serological test may be performed using an enzyme-linked immunosorbent assay or ELISA-based test. An ELISA assay uses a solid-phase type of enzyme immunoassay (EIA) to detect the presence of a protein in a liquid sample using antibodies directed against the protein to be measured. Detection may be accomplished by measuring the activity of the reporter enzyme via incubation with the appropriate substrate to produce a measurable product. ELISA-based serological testing protocols for viruses, such as but not limited to, SARS-CoV-2 have been established by the Center for Disease Control (see, for example, "Serology Testing for COVID-19 at CDC").

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
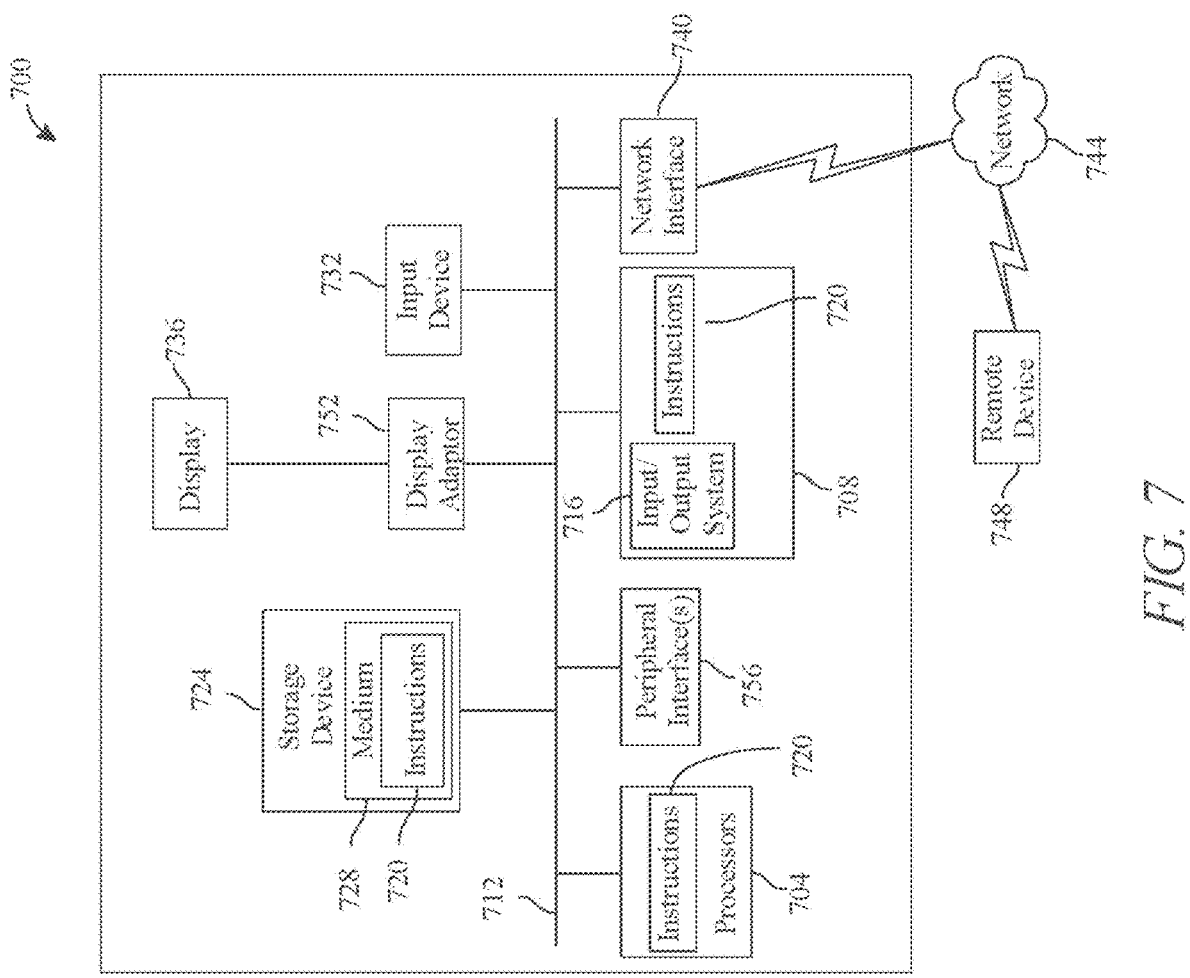
FIG. 7 is a block diagram of a computing system that can be used to implement any one or more of the methodologies disclosed herein and any one or more portions thereof.

FIG. 7 shows a diagrammatic representation of one embodiment of a computing device 304 in the exemplary form of a computer system 700 within which a set of instructions for causing a control system to perform any one or more of the aspects and/or methodologies of the present disclosure may be executed. It is also contemplated that multiple servers may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIREWIRE interface, a direct interface to bus 712, and any combinations thereof. Input device 732 may include a touch screen interface that may be a part of or separate from display device 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing device 304, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve embodiments according to this disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A method of classifying sample data for robotically extracted samples, the method comprising:
  receiving data related to a specimen from a human subject with a potential infection of a first disease agent, wherein the specimen comprises:
    genetic material collected from the human subject using a collection device and stored in a collection carrier; and
    a unique identifier on the collection carrier;
  retrieving, by a computing device, human subject descriptive data from an optical scanning device as a function of the unique identifier;
  classifying, at the computing device, the human subject descriptive data to identify a second disease agent, wherein classifying further comprises:
    generating a classifier using a first machine-learning process as a function of human subject descriptive training data, wherein the human subject descriptive training data correlates human subject descriptive data with a second disease agent; and
    generating the identity of the second disease agent as a function of the descriptive data and the classifier;
  processing, by the computing device, a sequence of genetic material from the specimen prepared by an automated robot; and
  obtaining, by the computing device, a test result determined by an analysis device for the first disease agent as a function of the sequence of genetic material.

2. The method of claim 1, wherein the collection device comprises:
  a swab; and
  a transfer medium, wherein the swab is dipped in the transfer medium.

3. The method of claim 1, wherein the collection device comprises blotting paper.

4. The method of claim 1, wherein the first disease agent further comprises a coronavirus.

5. The method of claim 1, further comprising determining a human subject contact profile,
  wherein determining the human subject contact profile further comprises:
    prompting a human subject for human subject intake data;
    receiving human subject intake data as a function of the prompting;
    generating a second machine learning process as a function of contact training data, wherein the contact training data correlates intake data elements with a human subject contact profile elements; and
    determining the human subject contact profile as a function of the intake data and the second machine-learning process.

6. The method of claim 1, wherein processing a sequence of genetic material from the specimen comprises:
  aggregating, by the automated robot, a plurality of human subject specimens from a plurality of human subject specimen into a single extraction.

7. The method of claim 1, wherein retrieving the human subject descriptive data further comprises:
  performing, by the computing device, a textual conversation with the user, the textual conversation including transmitting to a user client device a plurality of potential user symptoms; and
  receiving, at the computing device, a user selection of a potential user symptom from the plurality of user symptoms.

8. The method of claim 1, wherein the test result further comprises a positive test result, and
  further comprising:
    establishing communication including an authorized human subject contact, by the computer device, as a function of the positive test result; and initiating a conferencing event with the authorized contact.

9. The method of claim 1, wherein the second disease agent is identical to the first disease agent.

10. The method of claim 1 further comprising:
determining, by the computing device, a presence of the first disease agent and the second disease agent in the specimen, wherein the first disease agent has a different identity from the second disease agent; and
generating, by the computing device a recommendation for the human subject, based on the determination.

11. A system of classifying sample data for robotically extracted samples, the system comprising a computing device configured to:
receive data related to a specimen from a human subject with a potential infection of a first disease agent, wherein the specimen comprises:
genetic material collected from the human subject using a collection device and stored in a collection carrier; and
a unique identifier on the collection carrier;
retrieve human subject descriptive data from an optical scanning device as a function of the unique identifier;
classify the human subject descriptive data to identify a second disease agent, wherein classifying further comprises, further comprising:
generate a classifier using a first machine-learning process as a function of human subject descriptive training data, wherein the human subject descriptive training data correlates human subject descriptive data with a second disease agent; and
generate the identity of the second disease agent as a function of the descriptive data and the classifier;
process a sequence of genetic material from the specimen prepared using an automated robot; and
obtain a test result determined using an analysis device for the first disease agent as a function of the sequence of genetic material.

12. The system of claim 11, wherein the collection device comprises a swab; and
a transfer medium, wherein the swab is dipped in the transfer medium.

13. The system of claim 11, wherein the collection device comprises blotting paper.

14. The system of claim 11, wherein the first disease agent further comprises a coronavirus.

15. The system of claim 11, wherein the computing device is further configured to:
prompt a human subject for intake data; and
generate a second machine learning process as a function of the intake data, wherein the second machine-learning process uses intake data as an input and outputs a human subject contact profile.

16. The system of claim 11, wherein the computer device is further configured to process a sequence of genetic material from the specimen aggregated from a plurality of human specimens into a single extraction by the automated robot.

17. The system of claim 11, wherein the computing device is further configured to:
perform a textual conversation with the user, the textual conversation including transmitting to the computing device, a plurality of potential user symptoms and receiving a human subject selection of a potential user symptom from the plurality of user symptoms; and
receive a user selection of a potential user symptom form the plurality of user symptoms.

18. The system of 11, wherein the test result further comprises a positive test result, the computing device further configured to:
notify an authorized human subject contact of a positive test result; and
initiate a conferencing event with the authorized contact.

19. The system of claim 11, wherein the second disease agent is identical to the first disease agent.

20. The system of claim 11, wherein the computing device is further configured to:
determine a presence of the first disease agent and the second disease agent in the specimen, wherein the first disease agent has a different identity from the second disease agent; and
generate a recommendation for the human subject based on the determination.

\* \* \* \* \*